US007186410B2

(12) United States Patent
Chtourou et al.

(10) Patent No.: US 7,186,410 B2
(45) Date of Patent: Mar. 6, 2007

(54) METHOD FOR PREPARING HUMAN IMMUNOGLOBULIN CONCENTRATES FOR THERAPEUTIC USE

(75) Inventors: Abdessatar Sami Chtourou, Elancourt (FR); Philippe Paolantonacci, Gif sur Yvette (FR); Roland Schmitthaeusler, Montigny le Bretonneux (FR); Jacky Lirochon, Breuillet (FR)

(73) Assignee: Laboratoiore Francais du Fractionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 10/476,771

(22) PCT Filed: Apr. 24, 2002

(86) PCT No.: PCT/FR02/01407

§ 371 (c)(1),
(2), (4) Date: Feb. 13, 2004

(87) PCT Pub. No.: WO02/092632

PCT Pub. Date: Nov. 21, 2002

(65) Prior Publication Data

US 2004/0132979 A1 Jul. 8, 2004

(30) Foreign Application Priority Data

May 11, 2001 (FR) ................................. 01 06234

(51) Int. Cl.
*A61K 39/395* (2006.01)

(52) U.S. Cl. .............................. 424/176.1; 424/177.1; 530/387

(58) Field of Classification Search ................ 530/413; 424/176.1, 177.1
See application file for complete search history.

(56) References Cited

U.S. PATENT DOCUMENTS

| 4,272,521 A | * | 6/1981 | Zuffi | .................... 530/390.5 |
| 4,305,870 A | | 12/1981 | Liu et al. | |
| 5,075,425 A | | 12/1991 | Kotitschke et al. | |
| 5,258,177 A | * | 11/1993 | Uemura et al. | .......... 424/176.1 |
| 5,808,000 A | | 9/1998 | Mannhalter et al. | |
| 6,069,236 A | | 5/2000 | Burnouf-Radosevich et al. | |
| 6,096,872 A | * | 8/2000 | Van Holten et al. | ..... 530/390.1 |
| 6,150,507 A | * | 11/2000 | Houtchens et al. | ......... 530/385 |

FOREIGN PATENT DOCUMENTS

WO    WO 99/64462 A1    12/1999

OTHER PUBLICATIONS

Millipore validation document, Ensuring Regulatory Compliance, p. 12.*
Steinbuch et al., "Isolement De L'Immunoglobuline IgG Du Plasma Humain A L'Aide De L'Acide Caprylique", Extrait De La Revue Francaise De'Etudes Cliniques Et Biologiques, vol. 14, No. 10, 1969, pp. 1054-1058.

* cited by examiner

*Primary Examiner*—Christina Chan
*Assistant Examiner*—Yunsoo Kim
(74) *Attorney, Agent, or Firm*—Birch, Stewart, Kolasch & Birch, LLP

(57) ABSTRACT

The invention concerns a method for preparing human immunoglobulin concentrates for therapeutic use, from plasma or a plasma fraction. The method comprises pre-purification and a single anion-exchange chromatography carried out at alkaline pH, thereby enabling the immunoglobulins to be retained on the chromatographic support and fractionated. The method enables to obtain IgG, IgA and IgM concentrates.

33 Claims, No Drawings

METHOD FOR PREPARING HUMAN IMMUNOGLOBULIN CONCENTRATES FOR THERAPEUTIC USE

CROSS-REFERENCE TO RELATED APPLICATION

This application is the national phase under 35 U.S.C. § 371 of PCT International Application No. PCT/FR02/01407 which has an International filing date of Apr. 24, 2002, which designated the United States of America.

BACKGROUND OF THE INVENTION

1. Field of the Invention

The invention relates to a process for preparing human immunoglobulin concentrates for therapeutic use, from plasma or a fraction of human plasma. The process enables immunoglobulins G (IgG), immunoglobulins A (IgA) and immunoglobulins M (IgM) to be obtained.

2. Related Prior Art

The use of human plasma fractions enriched with immunoglobulins for the treatment of various infections or congenital deficiencies has been known since the development of the ethanol precipitation process by Cohn (Cohn et al. 1946, J. Am. Chem. Soc. 68, 459; Oncley et al., 1949, J. Am. Chem. Soc. 71, 541). As the therapeutic indications for immunoglobulins have grown in number, there is a need for a product offering ever increasing performance and purity.

The complexity of the structure of immunoglobulins (four polypeptidic chains joined by disulphide bonds) and the variety of antibodies present in the mixture of the plasma of several thousand donors are not presently factors favouring the biotechnological development of immunoglobulins. Although some monoclonal antibodies are produced by genetic engineering, their extreme specificity represents a drawback for therapeutic applications in which polyreactivity appears necessary.

In addition, numerous pathologies, in particular of autoimmune origin, are presently treated using IgG concentrates. This widespread use has led to a shortage in Europe and the United States over the last few years.

Furthermore, in these same pathologies, the efficiency of IgM-enriched preparations has recently been demonstrated (Hurez et al. Blood 90, 1997, 4004–4013), but there exists no preparation for therapeutic use that is sufficiently purified and that has a sufficient IgM concentration.

This is why the Applicant has devoted itself to the development of a new process for the preparation of human immunoglobulins. The process can be applied to a pool of serums (from at least 10 000 donors), which ensures the presence of all the antibodies normally present throughout the population of a chosen region, or to hyperimmune serums selected for their specific immunoglobulin content. The process further allows the preparation of IgA and IgM concentrates.

Numerous variants of the original Cohn process have been described. They propose, in addition to the selective precipitation of the proteins with ethanol, various additional treatments such as precipitation with polyethylene glycol, the gentle treatment with proteolytic enzymes, etc., intended to eliminate the aggregates of immunoglobulin polymers (liable to activate the complement system and to lead to anaphylactic reactions).

An alternative approach to ethanol precipitation is described by Steinbuch et al. (Rev. Franc. Et. Clin. et Biol. 1969, XIV, 1054); this approach uses precipitation with octanoic acid. This acid precipitates most of the proteins in the plasma and leaves the immunoglobulins in the supernatant. Purification of these immunoglobulins is continued by adsorption (in "batches") using an anion exchanger, DEAE-cellulose, which also leaves the immunoglobulins in the supernatant. The latter is then concentrated.

Various processes have also been developed for increasing the purity of the products through the use of chromatographic separation processes. Those yielding the best performance (in particular EP 0 703 922, WO 99/64462) include at least two successive chromatography steps, one using anion exchange and the other using cation exchange. The specificity of these processes is provided by the property of the anion exchangers of not adsorbing the immunoglobulins G, under conventional conditions of implementation, but of fixing most of the other proteins co-purified during the pre-purification steps.

Various purified IgG preparations are thus already available but their preparation processes still pose problems in terms of productivity and complexity of implementation on an industrial scale. These problems are further increased by the need to include in the process viral inactivation, involving an additional step to eliminate the virucidal agents used.

In addition, all of the processes presently described have been developed and optimised for the production of IgGs only.

SUMMARY OF THE INVENTION

The Applicant has found it to be possible to produce several concentrates of immunoglobulins by combining a pre-purification step and a single ion exchange chromatography step and thus implement a very simple process that is highly productive and compatible with a virucidal solvent-detergent treatment.

The process according to the present invention is thus applicable to blood plasma or to a fraction of blood plasma already enriched with immunoglobulins, and it includes pre-purification through the precipitation of lipidic and proteic contaminants and a single anion exchange chromatography step, carried out at an alkaline pH, which allows the adsorption of the immunoglobulins on the anion exchange chromatographic material.

Pre-purification is carried out by means of known precipitating agents such as octanoic acid, tricalcium phosphate or bentonite.

After this pre-purification step and prior to chromatography, the process includes a step of viral inactivation, preferably using solvent-detergent, according to a known method.

At the end of this treatment, the pre-purified filtrate and solvent-detergent mixture is subjected to chromatographic separation which is carried out using a DEAE, TMAE or QAE groups-grafted gel of cross-linked polysaccharide or vinyl polymer. This chromatography step includes:

adjusting to a pH of 8.9 to 9.1 the solution that has undergone the solvent-detergent treatment;

injecting it onto the chromatographic column previously equilibrated with buffer at a pH of 8.9 to 9.1, which permits adsorption of the immunoglobulins and allows the non-adsorbed proteins to flow through into the effluent;

washing with the same buffer until all the non-adsorbed proteins and the solvent-detergent mixture have been eliminated; and eluting the immunoglobulins with a suitable buffer.

Said elution can be carried out either with a phosphate buffer at a pH between 4 and 7, and preferably, at a pH of 6.2, to elute the immunoglobulins G, or sequentially:

initially, as above to elute the immunoglobulins G;

subsequently, using the same phosphate buffer to which has been added 100 to 175 mM NaCl, and preferably, 150 mM, at a pH of 6.0 to 6.3, to elute a fraction containing the IgAs and IgG4s.

The process can be continued by further elution with the same buffer adjusted to a pH of 6 to 7 to which has been added 250 to 350 mM NaCl, and preferably, 300 mM, to elute the IgMs.

The immunoglobulins thus eluted are harvested, concentrated by ultrafiltration and subjected to conventional sterile filtration, and then to filtration through nanometric filters of a porosity decreasing from 100 to 15 nanometers, in particular using three filters arranged in series and having decreasing thresholds of retention: 100, 50 and 20 nanometers. This nanofiltration enables viruses resistant to the solvent-detergent treatment to be eliminated.

A pharmaceutically acceptable stabilising agent is added to the concentrated and filtered solution of immunoglobulins, and the latter is then packaged as a sterile solution, and optionally deep-frozen and freeze-dried.

The following examples illustrate the invention without, however, limiting its scope.

DETAILED DESCRIPTION OF THE PREFERRED EMBODIMENTS

Example I

As a starting material, use is made of 1 kg of "I+II+III" precipitate obtained from plasma treated with ethanol according to the Cohn method (already mentioned) or the Kistler and Nitschmann method (1962, Vox Sang. 7, 414).

This precipitate is resuspended in acetate buffer (sodium acetate-acetic acid) at a pH of 4.7 to 4.9, with stirring, at 20° C.

Octanoic acid is added thereto up to a final concentration of 20 g/l. The acid should be added slowly, at ambient temperature.

To the mixture is added a filtration aid, and the precipitate is separated by filtration by means of a filter press.

The filtrate is recovered, clarified and concentrated by ultrafiltration, then it is subjected to sterile filtration at 0.45 µm and 0.2 µm.

It is then subjected to a solvent-detergent viral inactivation treatment as described by Neurath and Horowitz (U.S. Pat. No. 4,764,369).

A Triton® X 100 (octoxinol 10)/TnBP mixture is used.

The mixture is adjusted to 64 g/l of proteins, at a pH of 6.5. Contact is maintained for 4 to 6 hours, at between 4 and 25° C. Then, the pH is adjusted to 9 (with NaOH).

The mixture is then subjected to an anion exchange chromatography using a column.

A chromatographic column is filled with TMAE-Fractogel® used as an anion exchange material, equilibrated with a glycine-NaCl mixture (glycine: 0.676 g/l—NaCl: 0.526 g/l) at a pH of 9.

The mixture is injected onto the column in a proportion of 50 g of proteins per liter of gel.

Once this has been done, the column is washed with glycine-NaCl buffer at a pH of 9 (the same as for equilibrating purposes). The washing is monitored by the optical density of the effluent at 280 nm.

After reaching the base line optical density, the column is eluted with phosphate buffer at a pH of 6.2 (disodium hydrogen phosphate—sodium dihydrogen phosphate).

The eluate, containing the immunoglobulins G, is adjusted to a pH of 4.5 and subjected to ultrafiltration using cassettes.

The solution is then subjected to sterile filtration at 0.22 µm, and then to nanometric filtration using three filters arranged in series and having decreasing thresholds of retention: 100, 50 and 20 nanometers. Filtration is followed by ultrafiltration using a cassette to concentrate the final solution to 120–150 g/l.

The analysis results for three pilot batches are given in the following table.

TABLE I

| | PILOT BATCHES | | |
|---|---|---|---|
| | 00 ILP 043 PV | 00 ILP 044 PV | 00 ILP 045 PV |
| Polymers (%) | 0.19 | 0.19 | 0.07 |
| Dimers (%) | 3.29 | 2.27 | 2.15 |
| Monomers (%) | 96.52 | 97.54 | 97.78 |
| IgG (g/l) | 52.5 | 50.4 | 50.8 |
| IgG1 (g/l) | 31.6 | 29.9 | 29.2 |
| IgG2 (g/l) | 17.1 | 15.3 | 13.1 |
| IgG3 (g/l) | 1.19 | 1.07 | 0.96 |
| IgG4 (g/l) | 0.52 | 0.61 | 0.56 |
| IgM (µg/l) | 310 | 459 | 1795 |
| Anti-Hbs (IU/ml) | 10.2 | 10.3 | 9.4 |

Example II

As a starting material, use is made of 1670 g of "Precipitate II" obtained from 80 liters of plasma treated with ethanol according to the Cohn method.

This variant of the process makes it possible, in particular, to turn to good account type II precipitates deep frozen and stored before being subjected to further treatment.

This precipitate is resuspended in 9 kg of a water-NaCl mixture. The pH is adjusted to 6.2 with acetic acid.

15 g of tricalcium phosphate are added thereto as an adsorbing agent (for contaminants of the lipidic type, kallikrein, etc.).

After one hour of contact, a filtration aid is added to the mixture and the precipitate is separated by filtration by means of a filter press.

The filtrate is recovered, glycine (15 g/l) is added thereto, and is adjusted to a pH of 4.8 with acetic acid.

80 g of bentonite are added thereto as an adsorbing agent (in particular for the traces of activated clotting factors), with stirring for 30 minutes.

A filtration aid is added to the mixture and the precipitate is separated by filtration by means of a filter press.

The filtrate is recovered and concentrated by ultrafiltration.

The process is continued (by solvent-detergent treatment and chromatography), as in example I.

The analysis results for the three pilot batches are set out in the following table.

TABLE II

PILOT BATCHES

|  | 286 | 287 | 321 |
|---|---|---|---|
| Polymers (%) | 0.5 | 0.5 | <0.1 |
| Dimers (%) | 2.8 | 2.8 | 1.4 |
| Monomers (%) | 96.7 | 96.7 | 98.5 |
| IgG (g/l) | 51.8 | 53.2 | 61.3 |
| IgG1 (%) | 62.5 | 62.6 | 64.4 |
| IgG2 (%) | 33.0 | 33.0 | 32.2 |
| IgG3 (%) | 3.2 | 3.3 | 2.2 |
| IgG4 (%) | 1.2 | 1.2 | 0.8 |
| IgA (mg/l) | 26.4 | 21.5 | 12.6 |
| IgM (µg/l) | 90.8 | 69.4 | 123 |
| Anti-Hbs (IU/ml) | 147 | 122 | 8.6 |

Example III

The process is implemented in the same way as in example I, but the starting material is plasma (non precipitated with ethanol).

This variant is not advantageous from the productivity viewpoint but it is of interest (thanks to its small number of steps) in the treatment of plasmas that present particularly a high rare antibodies content.

Example IV

The process is implemented in the same way as in Example I, but the chromatographic column is sequentially eluted:

after the injection and the washing of the column, it is eluted with a first phosphate buffer at a pH of 6.2 to elute the IgGs as in example I;

next, it is eluted with the same buffer, to which has been added 150 mM NaCl, which elutes an IgA and IgG4-enriched fraction.

IgG4s appear to play a part in protection from parasitic infections and from allergies to pollens and mites.

Surprisingly, in their biochemical properties and their behaviour during ion exchange, they resemble immunoglobulins A.

Example V

The process is implemented in the same way as in example IV, but, after the second elution that produces the IgA-enriched fraction, 300 mM NaCl is added to the same buffer, which desorbs the IgMs. There is thus obtained a concentrated (80%) fraction of IgMs. These are concentrated and pharmaceutically acceptable stabilising agents are added thereto.

The production results for a batch of concentrated IgMs are set out in the following table.

TABLE III (IgM batch 2000-97)

| Fraction | Volume (ml) | Ig Totals (mg) | IgM (mg) | IgG (%) | IgA (%) | IgM (%) |
|---|---|---|---|---|---|---|
| Pre-purified Ig | 2190 | 39957 | 2037 | 92.6 | 2.2 | 5.1 |
| Fraction not adsorbed on the column | 3800 | 566.8 | <32.3 | 86.5 | <7.8 | <5.7 |
| Eluate 1 (IgG) | 2700 | 37374 | <22.9 | 99.8 | <0.1 | <0.1 |
| Eluate 2 (IgA) (0.15M NaCl) | 1350 | 3171 | 62.5 | 74.9 | 23.1 | 2 |
| Eluate 3 (IgM) (0.3M NaCl) | 114.5 | 1775.1 | 1545.7 | 6.2 | 6.8 | 87.1 |

The invention claimed is:

1. A process for preparing human immunoglobulin concentrates for therapeutic use, from blood plasma or a fraction of plasma enriched with immunoglobulins, which comprises pre-purification by precipitating lipidic and proteic contaminants and a single chromatography step carried out on an anion exchange chromatographic material at an alkaline pH, wherein said immunoglobulins are adsorbed on said anion exchange chromatographic material.

2. A process according to claim 1, wherein the pre-purification is carried out by means of at least one precipitating agent selected from the group consisting of octanoic acid, tricalcium phosphate and bentonite.

3. A process according to claim 1, wherein, after pre-purification and prior to chromatography, a viral inactivation treatment, is conducted using solvent-detergent.

4. A process according to claim 1, wherein chromatography is carried out using a DEAE, TMAE or QAE groups-grafted gel of cross-linked polysaccharide or vinyl polymer.

5. A process according to claim 1, wherein the chromatography step comprises:
   a) using immunoglobulins that have undergone the solvent-detergent treatment;
   b) adjusting the immunoglobulins to a pH of 8.9 to 9.1;
   c) injecting the immunoglobulins of step b) onto a chromatographic column previously equilibrated with buffer at a pH of 8.9 to 9.1, which permits adsorption of the immunoglobulins of step b) and allows the non-adsorbed proteins to flow through into the effluent;
   d) washing the chromatographic column with the same buffer until all the non-adsorbed proteins and the solvent-detergent mixture have been eliminated; and
   e) eluting the immunoglobulins with a suitable buffer.

6. A process according to claim 5, wherein the elution is carried out in one step, with a phosphate buffer at a pH between 4 and 7, and preferably, at a pH of 6.2, to elute the immunoglobulins G.

7. A process according to claim 5, wherein the elution is carried out sequentially,
   a) initially, using a phosphate buffer at a pH between 4 and 7, and preferably, at a pH of 6.2, to elute the immunoglobulins G;
   b) subsequently, using the same phosphate buffer to which has been added 100 to 175 mM NaCl, and preferably, 150 mM, at a pH of 6.0 to 6.3, to elute a fraction containing the IgAs and IgG4s.

8. A process according to claim 5, wherein the elution is carried out sequentially,
   a) initially, using a phosphate buffer at a pH between 4 and 7, and preferably, at a pH of 6.2, to elute the immunoglobulins G;
   b) sequentially, using the same phosphate buffer to which has been added 100 to 175 mM NaCl, and preferably, 150 mM, at a pH of 6.0 to 6.3, to elute a fraction containing the IgAs and IgG4s; and c) a further elution with the same buffer adjusted to a pH of 6 to 7 to which has been added 250 to 350 mM NaCl, and preferably, 300 mM, to elute the IgMs.

9. A process according to claim 1, wherein, after elution of the immunoglobulins, these are harvested, concentrated by ultrafiltration and subjected to conventional sterile filtration, and then to filtration through nanometric filters of a porosity decreasing from 100 to 15 nanometers.

10. A process according to claim 9, wherein a pharmaceutically acceptable stabilising agent is added to the concentrated and filtered solution of immunoglobulins, and then packaged as a sterile solution, and optionally deep-frozen and freeze-dried.

11. The process according to claim 2, wherein the precipitating agent is octanoic acid.

12. A process for preparing immunoglobulin concentrates from human blood plasma or an immunoglobulin-enriched blood plasma fraction, comprising:
    precipitating non-immunoglobulin lipidic and proteic contaminants from the blood plasma or immunoglobulin-enriched blood plasma fraction to make a pre-purified immunoglobulin solution;
    adjusting to alkaline pH both the pre-purified immunoglobulin solution and an anion exchange resin;
    exposing the alkaline, pre-purified immunoglobulin solution to the alkaline anion exchange resin whereby the immunoglobulins bind the anion exchange resin;
    washing the immunoglobulin bound anion exchange resin with a buffer to remove non-immunoglobulin contaminants; and
    eluting the immunoglobulins from the anion exchange resin with an elution buffer to produce an immunoglobulin eluate.

13. The process of claim 12, wherein said precipitating step is conducted with a precipitation agent that is at least one member selected from the group consisting of octanoic acid, tricalcium phosphate, and bentonite.

14. The process of claim 13, further comprising inactivating viruses by adding a solvent-detergent to the pre-purified immunoglobulin solution prior to exposing the alkaline, pre-purified immunoglobulin solution to the alkaline anion exchange resin.

15. The process of claim 14, wherein said anion exchange resin is at least one member selected from the group consisting of DEAE, TMAE, and QAE.

16. The process of claim 15, wherein the pre-purified immunoglobulin solution and the anion exchange resin are adjusted to a pH between 8.9 and 9.1.

17. The process of claim 16, wherein the alkaline, pre-purified immunoglobulin solution is combined with the anion exchange resin that has been packed in a column.

18. The process of claim 17, wherein immunoglobulins IgG1, IgG2, and IgG3 are selectively eluted from the anion exchange resin with a first phosphate elution buffer that has a pH between 4 and 7 and is free of NaCl.

19. The process of claim 17, wherein said first phosphate elution buffer has a pH of 6.2.

20. The process of claim 18, wherein, following IgG1, IgG2, and IgG3 elution, immunoglobulins IgG4 and IgA are selectively eluted from the anion exchange resin with a second phosphate elution buffer comprising 100 to 175 mM NaCl and a pH between 6.0 and 6.3.

21. The process of claim 20, wherein, said second phosphate elution buffer comprises 150 mM NaCl and a pH between 6.0 and 6.3.

22. The process of claim 21, wherein, following IgG4 and IgA elution, IgM immunoglobulins are selectively eluted from the anion exchange resin with a third phosphate elution buffer comprising 250 to 350 mM NaCl and a pH between 6 and 7.

23. The process of claim 12 or 22 further comprising:
    concentrating the immunoglobulin eluate by ultrafiltration; and
    sterilizing the thus produced concentrated immunoglobulin solution by filtering it through nanometric filters of a porosity decreasing from 100 to 15 nanometers.

24. The process of claim 23, further comprising:
    adding a pharmaceutically acceptable stabilising agent to the concentrated and sterilized immunoglobulin solution;
    packaging the stabilized, concentrated, and sterilized immunoglobulin solution; and
    deep-freezing or freeze-drying the stabilized, concentrated, and sterile immunoglobulin solution.

25. A process for preparing immunoglobulin concentrates from human blood plasma or an immunoglobulin-enriched blood plasma fraction, comprising:
    precipitating non-immunoglobulin lipidic and proteic contaminants from the blood plasma or immunoglobulin enriched blood plasma fraction;
    adjusting to alkaline pH both the pre-purified immunoglobulin solution and an anion exchange column;
    loading the alkaline, pre-purified immunoglobulin solution onto the alkaline anion exchange column whereby the immunoglobulins bind the anion exchange column;
    washing the immunoglobulin bound anion exchange resin with a buffer; and
    eluting sequentially from the immunoglobulin-bound anion exchange column three fractions wherein the first fraction contains immunoglobulins IgG1, IgG2, and IgG3 and is eluted with a first phosphate elution buffer comprsing a pH between 6.0 and 6.3 and free from NaCl, the second immunoglobulin fraction contains immunoglobulins IgG4 and IgA and is eluted with a second phosphate elution buffer comprising 150 to 175 mM NaCl and a pH between 6.0 and 6.3, and the third immunoglobulin fraction contains IgM immunoglobulins and is eluted with a third phosphate elution buffer comprising 250 to 350 mM NaCl and a pH between 6.0 and 6.3.

26. A process for preparing human immunoglobulin concentrates for therapeutic use, from blood plasma or a fraction of plasma enriched with immunoglobulins, which comprises pre-purification by precipitating lipidic and proteic contaminants and chromatography, the chromatography portion of said process consisting of a single chromatography step carried out on an anion exchange chromatographic material at an alkaline pH, which allows adsorption of the immunoglobulins on said anion exchange chromatographic material.

27. A process according to claim 26, wherein the pre-purification is carried out by means of at least one precipitating agent selected from the group consisting of octanoic acid, tricalcium phosphate and bentonite.

28. A process according to claim 26, wherein, after pre-purification and prior to chromatography, a viral inactivation treatment, is conducted using solvent-detergent.

29. A process according to claim 26, wherein chromatography is carried out using a DEAE, TMAE or QAE groups-grafted gel of cross-linked polysaccharide or vinyl polymer.

30. A process according to claim 26, wherein the chromatography step comprises:

a) using immunoglobulins that have undergone the solvent-detergent treatment;
b) adjusting the immunoglobulins to a pH of 8.9 to 9.1;
c) injecting the immunoglobulins of step b) onto a chromatographic column previously equilibrated with buffer at a pH of 8.9 to 9.1, which permits adsorption of the immunoglobulins of step b) and allows the non-adsorbed proteins to flow through into the effluent;
d) washing the chromatographic column with the same buffer until all the non-adsorbed proteins and the solvent-detergent mixture have been eliminated; and
e) eluting the immunoglobulins with a suitable buffer.

31. A process for preparing immunoglobulin concentrates from human blood plasma or an immunoglobulin-enriched blood plasma fraction, comprising:

precipitating non-immunoglobulin lipidic and proteic contaminants from the blood plasma or immunoglobulin-enriched blood plasma fraction to make a pre-purified immunoglobulin solution, said precipitating being conducted with a precipitation agent that is at least one member selected from the group consisting of octanoic acid, tricalcium phosphate, and bentonite;

adjusting to alkaline pH both the pre-purified immunoglobulin solution and an anion exchange resin;

inactivating viruses by adding a solvent-detergent to the pre-purified immunoglobulin solution;

exposing the alkaline, pre-purified immunoglobulin solution to the alkaline anion exchange resin at a pH between 8.9 and 9.1, whereby the immunoglobulins bind the anion exchange resin, wherein said anion exchange resin is at least one member selected from the group consisting of DEAE, TMAE, and QAE;

washing the immunoglobulin bound anion exchange resin with a buffer to remove non-immunoglobulin contaminants; and eluting the immunoglobulins from the anion exchange resin with an elution buffer to produce an immunoglobulin eluate.

32. The process of claim 31, wherein immunoglobulins IgG1, IgG2, and IgG3 are selectively eluted from the anion exchange resin with a first phosphate elution buffer that has a pH between 4 and 7 and is free of NaCl.

33. The process of claim 32, wherein, following IgG1, IgG2, and IgG3 elution, immunoglobulins IgG4 and IgA are selectively eluted from the anion exchange resin with a second phosphate elution buffer comprising 100 to 175 mM NaCl and a pH between 6.0 and 6.3.

* * * * *